Jan. 19, 1954 D. EVELEENS MAARSE Plant Pat. 1,242
SYRINGA VULGARIS PLANT
Filed Nov. 25, 1952
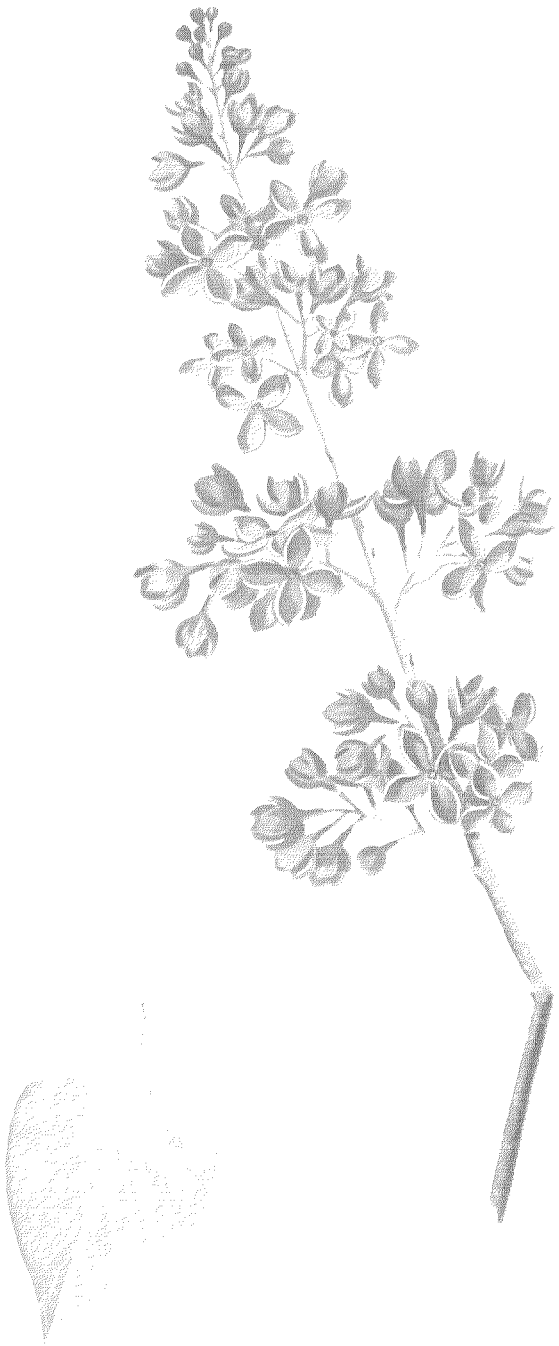
INVENTOR
Dirk Eveleens Maarse
By Orville M. Kile
Plant pat. Agt.

Patented Jan. 19, 1954 Plant Pat. 1,242

UNITED STATES PATENT OFFICE 1,242

SYRINGA VULGARIS PLANT

Dirk Eveleens Maarse, Aalsmeer, Netherlands, assignor of one-third to Anthonie Kluis, one-third to Johan Hendrik Kluis, and one-third to Frits Marie Kluis, all of Pompton Plains, N. J.

Application November 25, 1952, Serial No. 322,592

1 Claim. (Cl. 47—60)

My present discovery pertains to a new variety of *Syringa vulgaris* plant which is a sport of the variety Hugo de Vries (unpatented) and was discovered by me in my nurseries at Aalsmeer, Holland, during the course of my usual visits of inspection. The new variety has been asexually reproduced by me at the same location by means of budding and grafting, and its distinguishing features appear to be permanent.

I know of no variety similar to my own in coloring, but it is somewhat similar to its parent in other respects. My new variety has a flower which is two-toned, being lavender-purple with a narrow white rim or band around the edge of the petals or lobes.

The accompanying illustrations are water-color paintings of a cluster or panicle of the flowers in approximately their true colors and natural size. In the left-hand corner is a single leaf showing typical shape and approximately true color.

In the following detailed description, color plate numbers refer to Ridgway's Color Standards and Nomenclature.

*The plant*

Growth:

*Vigor and health.*—Very vigorous and healthy grower, the original plant having attained a height of about 6 feet since its discovery several years ago. Maximum height is as yet unknown.

Type: Erect bush or shrub, with long branches.

Blooming season: Mid-May or earlier, when grown in this climate.

Blooming habit:

*Borne.*—Flowers are borne in long, slender racimes or panicles with 10 to 14 opposite clusters of florets and a terminal cluster.

*Panicles.*—Panicles are mostly single but sometimes paired. They grow to be about 7 or 8 inches long, each panicle having 10 to 14 opposite clusters and a terminal cluster—each about 1½ inches long and containing from 4 to 8 florets.

*Progression of bloom.*—The lower pairs of clusters bloom first, progressing toward the terminal clusters until all or approximately all the florets are open and in good condition at the same time.

Stems:

*Main stems.*—Woody.

*New stems.*—Pliable but strong. Approximately Parrot Green (Pl. VI).

*Internodes.*—Internodes on new wood are short, being 1½ to 2 inches long.

Foliage:

*Quantity.*—Ample.

*Position.*—Opposite.

*Color.*—Slightly lighter than usual lilacs, being approximately Grass Green (Pl. VI) on upper surface and Oil Green (Pl. V) on under surface. Small, new leaves are russet-tinged.

*Size.*—Up to 3 inches long and approximately 2¼ to 2½ inches wide at broadest point.

*Surface.*—Smooth; slightly leathery to the touch.

*Texture.*—Normal.

*Leaf stem.*—Approximately 1 inch long.

*The bloom*

Buds:

*Color.*—Dark Perilla Purple (Pl. XXXVII) to Dark Maroon Purple (Pl. XXVI) when very small. As they begin to open they become lighter, or approximately Auricula Purple (Pl. XXVI) just before they begin to open.

*Form.*—Small, round pellet-like when first seen; later elongating.

Florets:

*Size.*—Including the calyx and tiny stem, the length of an opening floret is from ⅝ to ¾ inch; the diameter across the top of a fully opened floret is approximately 1 inch.

*Fragrance.*—Delicate and pleasing.

*Form.*—Has the usual single lilac form—long corolla-tube divided to make four lobes or petals. Petals are about half the length of the fully developed flower. Only the oldest florets open so that the lobes are at right angles to the corolla tube, and the petals or lobes remain cup-shaped until very old.

*Color.*—When the florets open wide they are a clear purple, approximately Dull Dark Purple (Pl. XXVI), with a rim or narrow band of white around the entire edge of each lobe or petal. This rim, being on the inner surface of the petal, is not visible in the early stages of opening but develops as the floret opens.

Having thus disclosed my discovery, I claim:

The new and distinct variety of *Syringa vulgaris* plant, substantially as herein shown and described, characterized particularly by its long, slender panicles with loosely arranged clusters of florets; its healthy and vigorous upright growth; its relatively light-green, cordate-shaped leaves; and its florets of clear purple with narrow, white band edging each lobe or petal.

DIRK EVELEENS MAARSE.

No references cited.